US00PP21619P2

(12) United States Plant Patent
Miyazaki

(10) Patent No.: US PP21,619 P2
(45) Date of Patent: Jan. 11, 2011

(54) ***MALCOLMIA* PLANT NAMED 'SUNMALPIN'**

(50) Latin Name: *Malcolmia maritima*
Varietal Denomination: Sunmalpin

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/587,444

(22) Filed: Oct. 7, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Malcolmia* plant named 'Sunmalpin', characterized by its upright and mounding plant habit; vigorous growth habit; freely branching and flowering plant habit; uniform and long flowering period; light pink-colored flowers; and good garden performance.

1 Drawing Sheet

Cultivar denomination: *Malcolmia maritima.*
Cultivar denomination: 'SUNMALPIN'.

BACKGROUND OF THE INVENTION

The present invention relates to a new and distinct cultivar of *Malcolmia* plant, botanically known as *Malcolmia maritima* and hereinafter referred to by the name 'Sunmalpin'.

The new *Malcolmia* plant is a product of a planned breeding program conducted by the Inventor in Higashiomi, Shiga, Japan. The objective of the breeding program is to develop new upright and mounding *Malcolmia* plants with long flowering time, winter hardiness, and attractive and uniform flower coloration.

The new *Malcolmia* plant originated from a cross-pollination conducted by the Inventor in Higashiomi, Shiga, Japan in March, 2004 of a proprietary selection of *Malcolmia maritima* identified as code number 3AK-18a, not patented, as the female, or seed, parent with a proprietary selection of *Malcolmia maritima* identified as code number 3AK-20, not patented, as the male, or pollen, parent. The new *Malcolmia* plant was discovered and selected by the Inventor as a single flowering plant from within the progeny of the stated cross-pollination in a controlled greenhouse environment in Higashiomi, Shiga, Japan in December, 2004.

Asexual reproduction of the new *Malcolmia* plant by vegetative cuttings in a controlled greenhouse environment in Higashiomi, Shiga, Japan since January, 2005, has shown that the unique features of this new *Malcolmia* plant are stable and reproduced true to type in successive generations.

SUMMARY OF THE INVENTION

Plants of the new *Malcolmia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunmalpin'. These characteristics in combination distinguish 'Sunmalpin' as a new and distinct cultivar of *Malcolmia:*

1. Upright and mounding plant habit.

2. Vigorous growth habit.
3. Freely branching and flowering plant habit.
4. Uniform and long flowering period.
5. Light pink-colored flowers.
6. Good garden performance.

Plants of the new *Malcolmia* can be compared to plants of the female parent selection. Plants of the new *Malcolmia* differ primarily from plants of the female parent selection in the following characteristics:

1. Plants of the new *Malcolmia* are more freely branching than plants of the female parent selection.
2. Plants of the new *Malcolmia* have larger flowers than plants of the female parent selection.

Plants of the new *Malcolmia* can be compared to plants of the male parent selection. Plants of the new *Malcolmia* differ primarily from plants of the male parent selection in plant form as plants of the new *Malcolmia* have shorter internodes and are denser than plants of the male parent selection.

Plants of the new *Malcolmia* can also be compared to plants of *Malcolmia maritima* 'Virginian Stock', not patented. In side-by-side comparisons conducted in Higashiomi, Shiga, Japan, plants of the new *Malcolmia* and 'Virginian Stock' differed primarily in the following characteristics:

1. Plants of the new *Malcolmia* were more freely branching and denser than plants of 'Virginian Stock'.
2. Plants of the new *Malcolmia* had shorter lateral branches than plants of 'Virginian Stock'.
3. Plants of the new *Malcolmia* had shorter leaves and petioles than plants of 'Virginian Stock'.
4. Plants of the new *Malcolmia* were more freely flowering than plants of 'Virginian Stock'.
5. Plants of the new *Malcolmia* and 'Virginian Stock' differed in flower color.

BRIEF DESCRIPTION OF THE PHOTOGRAPHS

The accompanying colored photographs illustrate the overall appearance of the new *Malcolmia* plant, showing the colors as true as it is reasonably possible to obtain in colored reproductions of this type. Colors in the photographs may differ slightly from the color values cited in the detailed botanical description which accurately describe the colors of the new *Malcolmia* plant.

The photograph at the top of the sheet comprises a side perspective view of a typical flowering plant of 'Sunmalpin' grown in a container.

The photograph at the bottom of the sheet is a close-up view of typical flowers of 'Sunmalpin'.

DETAILED BOTANICAL DESCRIPTION

The aforementioned photographs and following observations, measurements and values describe plants grown in 15-cm containers in Higashiomi, Shiga, Japan, under commercial practice during the autumn and winter in a polyethylene-covered greenhouse. During the production of the plants, day temperatures averaged 10° C. and night temperatures averaged 5° C. Plants had been growing for four months when the description and photographs were taken. In the following description, color references are made to The Royal Horticultural Society Colour Chart, 2001 Edition, except where general terms of ordinary dictionary significance are used.

Botanical classification: *Malcolmia maritima* 'Sunmalpin'.

Parentage:

*Female, or seed, parent.*—Proprietary selection of *Malcolmia maritima* identified as code number 3AK-18a, not patented.

*Male, or pollen, parent.*—Proprietary selection of *Malcolmia maritima* identified as code number 3AK-20, not patented.

Propagation:

*Type.*—By vegetative cuttings.

*Time to initiate roots, summer.*—About ten days at 25° C.

*Time to initiate roots, winter.*—About eight days at 18° C.

*Time to produce a rooted young plant, summer.*—About 30 days at 25° C.

*Time to produce a rooted young plant, winter.*—About 40 days at 18° C.

*Root description.*—Fine, fibrous; white in color.

*Rooting habit.*—Freely branching.

Plant description:

*Plant and growth habit.*—Upright and mounding plant habit; freely branching habit with numerous lateral branches developing per plant; pinching enhances lateral branch development; vigorous growth habit.

*Plant height.*—About 25 cm.

*Plant diameter.*—About 48.8 cm.

Lateral branch description:

*Length.*—About 11.8 cm.

*Diameter.*—About 2.4 mm.

*Internode length.*—About 1 cm.

*Strength.*—Strong.

*Aspect.*—Upright to decumbent.

*Texture.*—Pubescent.

*Color.*—Close to 144A tinted with close to N200A.

Foliage description:

*Arrangement.*—Alternate, simple.

*Length.*—About 3.2 cm.

*Width.*—About 1.7 cm.

*Shape.*—Elliptic.

*Apex.*—Rounded to truncate.

*Base.*—Cuneate.

*Margin.*—Entire, shallow lobing.

*Texture, upper and lower surfaces.*—Pubescent.

*Venation pattern.*—Pinnate; reticulate.

*Color.*—Developing and fully expanded leaves, upper surface: Close to 137B; venation, close to 144B. Developing and fully expanded leaves, lower surface: Close to 144A; venation, close to 144B.

*Petiole.*—Length: About 1.6 cm. Diameter: About 1.6 mm. Texture, upper and lower surfaces: Pubescent. Color, upper and lower surfaces: Close to 144B.

Lower description:

*Flower arrangement and habit.*—Single cruciate flowers arranged in racemes arising from upper leaf axils; freely flowering habit with usually about 50 flowers per plant at one time; flowers face upright.

*Fragrance.*—Moderately fragrant.

*Natural flowering season.*—Early flowering habit, plants of the new *Malcolmia* initiate and develop flowers about four to five weeks after planting; long flowering period; flowering commences naturally during the late autumn and plants flower continuously throughout the winter until late spring in Japan.

*Flower longevity.*—Individual flowers last about one week on the plant at temperatures of about 10° C.; flowers not persistent.

*Inflorescence diameter.*—About 5 cm.

*Flower diameter.*—About 2.3 cm.

*Flower length (depth).*—About 1.4 cm.

*Flower bud.*—Shape: Narrowly elliptical. Length: About 1 cm. Diameter: About 2.3 mm. Color: Close to 144A.

*Corolla.*—Petal quantity: Four per flower. Petal length: About 1.1 cm. Petal width: About 9 mm. Petal shape: Cordate. Petal apex: Cordate. Petal margin: Entire. Petal texture, upper and lower surfaces: Smooth, glabrous. Petal color: When opening, upper surface: Close to 77C to 77D; venation, close to 77A; towards the center, close to N144C; center, close to 145D. When opening, lower surface: Close to 76B. Fully opened, upper surface: Close to 76B; venation, close to 77B; towards the center, close to N144C; center, close to 145D. Fully opened, lower surface: Close to 76C.

*Claw.*—Length: About 1.3 cm. Width: About 1.1 cm. Texture: Smooth, glabrous. Color: Close to 145B.

*Calyx.*—Arrangement: Calyx tube with four sepals fused at the base. Sepal length: About 1 cm. Sepal width: About 1.3 mm. Sepal shape: Lanceolate. Sepal apex: Acute. Sepal margin: Entire. Sepal texture, upper and lower surfaces: Pubescent. Sepal color: Immature and mature, upper surface: Close to 144B. Immature and mature, lower surface: Close to 144B.

*Pedicels.*—Length: About 7 mm. Diameter: About 0.6 mm. Angle: Upright. Strength: Strong. Texture: Pubescent. Color: Close to 137C.

*Reproductive organs.*—Stamens: Quantity/arrangement: Six per flower. Stamen length: About 1.1 cm. Anther shape: Lanceolate. Anther size: About 3 mm by 0.5 mm. Anther color: Close to 5C. Pollen amount: Moderate. Pollen color: Close to 5C. Pistils: Quantity: One per flower. Pistil length: About 1.2 cm. Style color: Close to 147D. Stigma shape: Lanceolate. Stigma color: Close to 1C. Ovary color: Close to 137B. Seed/fruit: Seed and fruit development have not been observed on plants of the new *Malcolmia*.

Garden performance: Plants of the new *Malcolmia* have been observed to have good garden performance and to tolerate wind, rain and temperatures ranging from about −5° C. to about 25° C.

Pathogen/pest resistance: Plants of the new *Malcolmia* have not been observed to be resistant to pests and pathogens common to *Malcolmia*.

It is claimed:

1. A new and distinct *Malcolmia* plant named 'Sunmalpin' as illustrated and described.

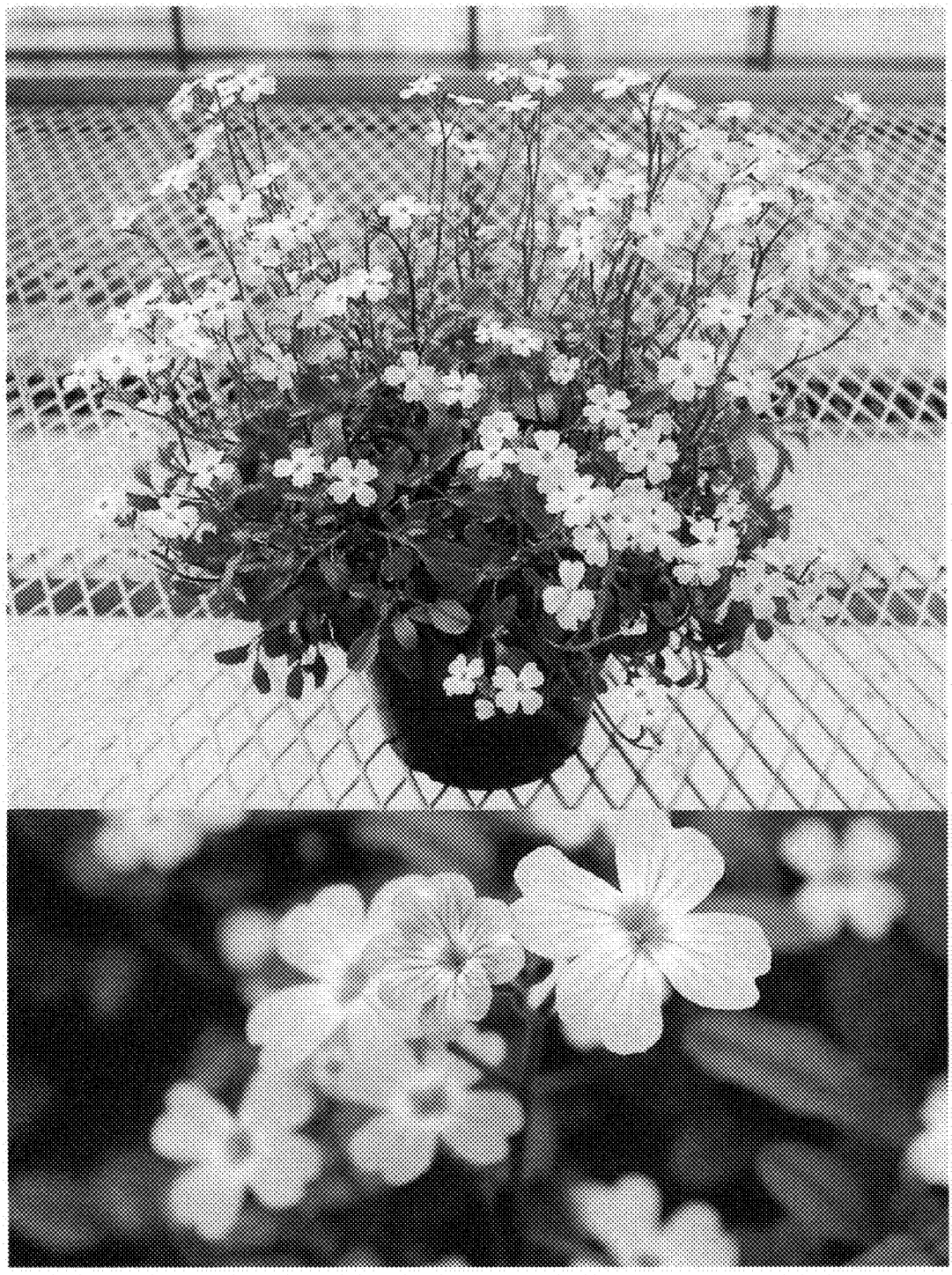

* * * * *